(12) United States Patent
Sato et al.

(10) Patent No.: US 6,419,930 B2
(45) Date of Patent: Jul. 16, 2002

(54) PHARMACOLOGICAL COMPOSITION HAVING BLOOD PRESSURE REDUCTIVE ACTIVITY

(75) Inventors: Taku Sato, Takasaki; Nobuhito Shiragaki; Tomoe Kawatsu, both of Samukawamachi; Toshihiko Hori, Yokohama, all of (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/820,997

(22) Filed: Mar. 30, 2001

(30) Foreign Application Priority Data

May 12, 2000 (JP) ........................................ 2000-139889
Aug. 30, 2000 (JP) ........................................ 2000-261356

(51) Int. Cl.$^7$ .......................... A61K 39/385; A23L 1/28; A01G 1/04
(52) U.S. Cl. ........................ 424/195.11; 47/1.1; 426/60; 426/61; 426/435; 426/590; 426/592; 426/597; 435/254.1
(58) Field of Search .................. 424/195.15; 435/254.1; 426/60, 61, 655, 597, 590, 592, 435; 47/1.1

(56) References Cited

FOREIGN PATENT DOCUMENTS

| JP | B-59/29221 | 7/1984 |
| JP | A-7/25774 | 1/1995 |
| JP | A-8/23938 | 1/1996 |

OTHER PUBLICATIONS

Computer JPAB Abstract JP2000300066 Sato "Culture of Mycoleptodonoides Aitchisonii" Oct. 31, 2000.*
Computer JPAB Abstract JP 409124541 Kawagishi et al May 13, 1997.*

Takashi Mizuno, Masamitsu Kawai, "Chemistry and Biochemistry of mushroom", Japan Scientific Societies Press (JSSP), 49–51, (1992).

Shunro Kawakishi, "Methods in Biochemistry Series No. 38," "Experimental Methods for Food Factors which Contribute to Prevention of Diseases by Modulating Physiological Systems of Human Body", Japan Scientific Societies Press (JSSP), 116–119, (1196).

*Bulletin of the Nagano Prefectural Forestry Research Institute* No. 3, 32–37 (1987).

*Bulletin of the Fukushima Prefectural Forest Experiment Station* No. 23, 81–101 (1990).

*Journal of the Food Hygienics Society of Japan* vol. 40, No. 5, 368–374 (1999).

*The Shokuhin Ryutsu Gijutsu*, vol. 18, No. 1, 17–21 (1989).

* cited by examiner

*Primary Examiner*—Herbert J. Lilling
(74) *Attorney, Agent, or Firm*—Venable; Robert Kinberg; Ann S. Hobbs (57) ABSTRACT

A pharmacological composition including a component having pressure reductive activity obtained from *Mycoleptodonoides aitchisonii* fruit body which is safe and cheap, harvested constantly year-round by artificial cultivation, with equal quality, and useful for prevention and/or amelioration of symptom of hypertension caused by angiotensin I converting enzyme or the like. The invention also includes foods or beverages containing the pharmacological compositions, and methods of preventing or treating hypertension by administration of the composition.

13 Claims, 1 Drawing Sheet

FIG. 1

PHARMACOLOGICAL COMPOSITION HAVING BLOOD PRESSURE REDUCTIVE ACTIVITY

FIELD OF THE INVENTION

The present invention relates to a pharmacological composition comprising a. component obtained from fruit body of *Mycoleptodonoides aitchisonii* (Bunaharitake: Japanese name) which has blood pressure reductive activity. Especially, it relates to a pharmacological composition including extract juice or extract obtained as an effective component from fruit body of Mycoleptodonoides aitchisonii that shows pressure reductive activity. It also relates to food and beverage including the mentioned pharmacological composition for prevention of hypertension and/or amelioration of its symptoms.

PRIOR ART

Mushrooms (Basidiomycota) have long been known to have various medicinal effects. Pressure reductive effect is one of those. For example, hydrothermal extract of Ganoderma lucidum (Reishiba: Japanese name) fruit body shows pressure reductive activity and its effective component is thought to be a high-molecular composition including amino acids of 100,000 molecular weight or more. Repression of vasopressor activity or pressure reductive activity is observed when feed stuff including Lentinus edodes (Shiitake: Japanese name) or Grifola frondosa (Maitake: Japanese name) is injected to animals. The effective component for which has not been made clear yet, still it is thought as a result of affecting lipid metabolism. Further, in case of Fomitopsis pincicola (Tsugasarunokoshikake: Japanese name), an agent, which is likely to be a mixed component of polysaccharide or proteoglycan the molecular weight of which is 600,000 or more, is reported to have shown pressure reductive activity while its functioning mechanism is unknown. Udenon, which is a tyrosine-hydroxylase inhibiting component of Oudemansiella radicata (Tsuetake: Japanese name), and oosponol, which is a dopamine β-hydroxylase inhibiting component of Gloeophyl lumsepiarium (Kikaigaratake: Japanese name) family demonstrate pressure reductive activity. This functional mechanism is considered to be based on β-receptor stimulation that is caused by repressing biosynthesis of catecholamine (Takashi Mizuno, Masamitsu Kawai, "Chemistry and Biochemistry of mushroom", Japan Scientific Societies Press (JSSP), 49–51, 1992).

Further, it is reported that extract juice of various food have angiotensin I converting enzyme (ACE) inhibiting activity (Shunro Kawakishi, Methods in Biochemistry Series No. 38, "Experimental Methods for Food Factors which Contribute to Prevention of Diseases by Modulating Physiological Systems of Human Body", Japan Scientific Societies Press (JSSP), 116–119, 1996). ACE is hypertension system enzyme which cuts off inactive His-Leu,in C-terminal of angiotensin I and develops angiotensin II having strong vasopressor activity such as vasoconstriction, on the other hand, ACE decomposes bradykinin having intense vasoditator activity. Hypertension can be treated by inhibiting ACE. Further attempts are proposed to manufacture functional beverage using extract juice or extract obtained from mushrooms having pharmacological function. For example, health-care drink including Grifola frondosa extract of Japanese Patent Publication No. 59-29221, Medicinal beverage including Shikateke extract of Japanese Laid-Open Patent Application No. 07-25774, and Agaricus blazei extract beverage of Japanese Laid-Open Patent Application No. 08-23938 are disclosed respectively. As is known from these prior arts, extracting methods to efficiently extract effective components of mushrooms varies depending on cultivar of material mushrooms, the properties of effective component and on the object of extraction or the like. Especially it is necessary to effectively prevent development off locks or browning or the like during storage when manufacturing beverage with the extracts. There is also a problem that since mushroom extracts have particular flavor which defect palatability depending on other materials. used together. Because of these problems, various devisals are made in preparation of extract for beverage.

On the other hand, *Mycoleptodonoides aitchisonii* (Kamiharitake: Local name) is known to grow in nature around September to early November in a manner as to piling up on fallen or stand-dead beech or Mongolian oak trees. It is also known that it's umbrella has the diameter of 3 to 10 cm with semi-circular shape and white colored, which later turns yellowish; that undersurface of the umbrella is white with needle-like structure and is later, like the upper surface, turns yellowish; that it's flesh is white, soft, and spongy; and that it has a unique flavor. Additionally, the mushroom is known to be rich in taste and very delicious. The study concerning cultivation using material trees such as beech or cherry is reported as artificial cultivation method of *Mycoleptodonoides aitchisonii* in "Bulletin of the Nagano Prefectural Forestry Research Institute", No. 3, 32–37, (1987) and in "Bulletin of the Fukushima Prefectural Forest Experiment Station", No. 23, 81–101, (1990). The study of cultivation method by means of cultivation of material trees and sawdust is reported in "THE SHOKUHIN RYUTSU GIJUTSU", Vol.18, No. 1, 17–21, (1989). According to these reports, while it is possible to harvest fruit body by material tree cultivation, there are difficulties that many material trees are necessary and that it is hard to cultivate wood-chip spawn on a block of wood because of strong rotting potential of hyphae. On the other hand, many cases of deformity are seen in container cultivation using sawdust and it is hard to harvest fruit body in package cultivation using sawdust. In any case, fungi bed cultivation is thought impossible with the current technology.

Further, there is a report that methanol extract of *Mycoleptodonoides aitchisonii* growing wild has anti-inflammation activity (Journal of the Food Hygienics Society of Japan, Vol. 40, No. 5, 368–374, 1999). It has been, however, unknown that there exists a component in *Mycoleptodonoides aitchisonii* fruit body having ACE inhibiting activity and pressure reductive activity. It has also been unknown that extract juice or extract can be obtained from Mycoleptodonoides aitchisonii fruit body having ACE inhibiting activity and pressure reductive activity. Still further, it has been unknown that pharmacological component can be obtained with stability having pressure reductive activity by using artificially cultivated, especially fungi bed cultivated, Mycoleptodonoides aitchisonii fruit body.

Problem to be Solved by the Invention

About half of over 60-year-old population in our country has hypertension or pre-hypertension, thus pressure reductive substances for food material that are safe and cheap are required. The object of the present invention is to provide a pharmacological composition including pressure reductive activity obtained from *Mycoleptodonoides aitchisonii* fruit body, especially a pharmacological composition including extract juice or extract having pressure reductive activity obtained as an effective a component from *Mycoleptodonoides aitchisonii* fruit body. The object is also to provide the above mentioned pharmacological composition obtained from Mycoleptodonoides aitchisonii fruit body that are not only safe and cheap but can be harvested constantly year-round and with same quality by artificial cultivation, and to provide food or beverage for prevention and/or symptom amelioration of hypertension including those pharmacological composition, for example, functional beverage with pressure reductive activity as well as excellent palatability.

Means to Solve the Problem

The present inventors have made a keen study to solve the above mentioned problems and have found existence of a component in *Mycoleptodonoides aitchisonii* fruit body, which only shows significant pressure reductive activity to hypertension model animals and not to normal model animals. Further they confirmed that beverage, wherein development of flocks or browning can be repressed, can be manufactured by using the above-mentioned extract juice or extract, while retaining the pressure reductive activity. The present invention is completed based on these findings.

The present invention relates to a pharmacological composition characterized in that it includes a component having pressure reductive activity obtained from *Mycoleptodonoides aitchisonii* fruit body (claim 1), also relates to; the pharmacological composition according to claim 1 characterized in that the pharmacological composition which includes a component having pressure reductive activity obtained from *Mycoleptodonoides aitchisonii* fruit body comprises, as an effective component, extract juice or extract having pressure reductive activity obtained from *Mycoleptodonoides aitchisonii* fruit body (claim 2); the pharmacological composition according to claim 2 characterized in that the extract juice or the extract is obtained by hydrothermal extraction of the fruit body (claim 3); the pharmacological composition according to claim 2, characterized in that dried fruit body is used as the fruit body (claim 4); the pharmacological composition according to claim 2, characterized in that the extract juice or extract underwent purifying treatment after hydrothermal extraction (claim 5); the pharmacological composition according to claim 5, characterized in that the purifying treatment is bentonite treatment and/or alcohol treatment (claim 6); the pharmacological composition according to claim 1, characterized in that *Mycoleptodonoides aitchisonii* fruit body is obtained from artificial cultivation (claim 7); the pharmacological composition according to claim 7, characterized in that the artificial cultivation is fungi bed cultivation (claim 8); the pharmacological composition according to claim 8, characterized in that the fungi bed cultivation consists of: sterilization step in which medium consists of mixture of water-keeping agent, culture substrate comprising at least one nutrient from dried okara or brewer's grains, and water is sterilized: inoculation step in which seed-fungi of *Mycoleptodonoides aitchisonii* is inoculated into the sterilized medium: early period of culture step in which medium inoculated with seed-fungi of *Mycoleptodonoides aitchisonii* is cultured to get fungi bed where hyphae have grown on the medium: middle course of culture step in which *Mycoleptodonoides aitchisonii* primordium, not exposed to physical space where it can grow to fruit body, is obtained from culture of the fungi bed: and late period of culture step in which the primordium selected from the *Mycoleptodonoides aitchisonii* primordium not exposed to physical space where it can grow to the fruit body, is cultured under the condition where *Mycoleptodonoides aitchisonii* primordium is exposed to physical space where it can grow to fruit body to obtain *Mycoleptodonoides aitchisonii* fruit body (claim 8); and the pharmacological composition according to claim 1, characterized in that at least a part of the pressure reductive activity is the pressure reductive activity by angiotensin I converting enzyme inhibiting activity (claim 9).

Further, the present invention relates to food or beverage for prevention and/or amelioration of hypertension, characterized in that the food or beverage includes a pharmacological composition according to any one of claims 1 to 9, and to food or beverage for prevention and/or amelioration of hypertension according to claim 10, characterized in that the food or beverage is beverage selected from tea beverage, nutrient drinks, fruit/vegetable beverage, calbonic acid beverage, low-calorie beverage, and alcoholic beverage (claim 10). The present invention still further relates to a prevention method of hypertension characterized in that the pharmacological composition according to any one of claims 1 to 9 is orally administrated to a normal human (claim 12) and a treatment method of hypertension characterized in that the pharmacological composition according to any one of claims 1 to 9 is orally administrated to a hypertension patient (claim 13).

The Mode of Embodiment of the Invention

Either of wild fruit body in nature or artificially cultivated fruit body may be used as *Mycoleptodonoides aitchisonii* fruit body of the invention, still artificially cultivated fruit body whose quality such as the quantity of the component and the like are constant is more preferable. Amount of component etc. vary depending on growing region or climate and so on in wild *Mycoleptodonoides aitchisonii* fruit body in nature, what is more, constant harvest year-round can hardly be achieved. On the contrary, not only amount of component is not affected by growing region or climate etc., but also constant harvest year-round is possible in artificially cultivated *Mycoleptodonoides aitchisonii* fruit body. Though methods of artificial cultivation are not limited, fungi bed cultivation is more preferable than material tree cultivation since constant harvest of *Mycoleptodonoides aitchisonii* year-round at low cost with equal quality and quantity of the component etc. is possible. Fungi bed cultivation here means a cultivation method in which seed-fungi is inoculated into substrate consists of water-keeping agent and nutrients, and then cultivated under circumstances where temperature, humidity and illuminance etc. are controlled without using material trees.

As a preferable mode of fungi bed cultivation, an artificial cultivation is concretely exemplified which consists of following steps. Sterilization step in which medium consists of water-keeping agent, culture substrate comprising at least one nutrient from dried okara, or brewer's grains, and water is sterilized. Inoculation step in which seed-fungi of *Mycoleptodonoides aitchisonii* is inoculated into the sterilized medium. Early period of culture step in which medium inoculated with seed-fungi of *Mycoleptodonoides aitchisonii* is cultured to get fungi bed where hyphae have grown on the medium. Middle course of culture step in which *Mycoleptodonoides aitchisonii* primordium, not exposed to physical space where it can grow to fruit body, is obtained from culture of the fungi bed. And late period of culture step in which the primordium, selected from the *Mycoleptodonoides aitchisonii* primordium not exposed to physical space where it can grow to the fruit body, is cultured under the condition where *Mycoleptodonoides aitchisonii* primordium is exposed to physical space where it can grow to fruit body to obtain *Mycoleptodonoides aitchisonii* fruit body. Here, physical space where *Mycoleptodonoides aitchisonii* can grow to fruit body means space where fruit body grows extending to outward from culture substrate. For example, when culture substrate is hermetically sealed with a plastic bag or the like, it means exterior space of the sealed container.

Any fungi strain such as commercially obtained strains or wild strains or whatever may be used as *Mycoleptodonoides aitchisonii* fungi strain of the invention as long as it belongs to *Mycoleptodonoides aitchisonii* whose fruit body includes component having pressure reductive activity. Still, it is especially preferable to use *Mycoleptodonoides aitchisonii* BNH-3 strain which is superior in its hypha growing capacity and primordium forming capacity. *Mycoleptodonoides aitchisonii* BNH-3 strain is purified and separated by the present inventor from fruit body growing wild on dead tree in the mountains in Minami-Akita Gun, Akita Prefecture. The culture obtained from potato dextrose agar slant culture can be stored at temperature of about 4° C. It is preferable to successively cultivate the stored strain within 3 to 6 months. Morphological properties of the fungi strain's fruit body, hypha, and spore are described as follows: Fruit body grows gregarious. The umbrella is scallop-shaped or paddle-shaped with a dimension of 3 to 8×3 to 10 cm. Its surface is hairless and smooth, white in color or little yellowish. Its flesh is white with thickness of 2 to 5 mm, edge of which is thin and somewhat dentational. Its hypha formation is a 2-hypha type having thick membrane hypha with the width of 4 to 10 $\mu$m, and thin membrane hypha with the width of 3.5 to 5 $\mu$m which is puffing and twisting. Its spore is a sausage-shape, colorless with the dimension of 2 to 2.5×5 to 6.5 $\mu$m.

Based on the above morphological properties and according to "Colored illustrated book of Japanese novel fungi II" written by Mutsuya Imazeki and Tsugio Hongo (first published May 31, 1989: Hoiku-sha), the fungi obviously belongs to *Mycoleptodonoides aitchisonii*. Under the Budapest Treaty concerning the international acknowledgement for microbe adoption as a procedure for patent application, the fungi is adopted as FERM BP-6697 to National Institute of Bioscience and Human-Technology, Agency of Industrial Science and Technology M.I.T.I., 1–3, Higashi 1-chome, Tsukuba-city, Ibaraki-prefecture, Japan on Apr. 7, 1999.

As water-keeping agents used for medium when *Mycoleptodonoides aitchisonii* is fungi-bed cultivated, the followings are exemplified: conifer derived sawdust such as cedar, hinoki cypress, or pine sawdust or the like: broadleaf derived sawdust such as beech, oak or sawtooth oak sawdust or the like: Corn Cobs (crushed corn axis) which has been used as an alternative sawdust for mushroom cultivation in recent years: and commercially available fungi bed materials and so on. All these may be used alone or used as a mixture of more than one kind.

Further, as cultivation nutrients for medium in fungi bed cultivation of *Mycoleptodonoides aitchisonii*, indispensable nutrient which is either one of brewer's grains or dried okara is used combined with nutrients other than the selected indispensable nutrient. As other nutrients, komenuka (rice bran), general fusuma (wheat bran), senkan wheat bran, and corn bran and the like, which are generally used in mushroom cultivation, are exemplified. When cultivation nutrient including neither brewer's grains nor dried okara is used as medium, not only hypha growth is slow but also it is hard to harvest fruit body with excellent size or shape.

Preferable mixture ratio of the above water-keeping agent and cultivation nutrient is that ranging from 10:0.7 to 10:4 in wet weight ratio, especially range between 10:2–3 is most preferable. Further, water level contained in final medium may be prepared ranging from 60 to 70%, about 65% is much preferable. Still further, soy bean skin, dried yeast, or pH adjuster or the like that are generally used in mushroom cultivation may be added as medium ingredients.

Fungi bed cultivation, as aforementioned, adopts three steps of cultivation that are early period of culture step, middle course of culture step, and late period of culture step. Early period of culture step is a step in which *Mycoleptodonoides aitchisonii* hyphae are grown enough on the medium under the specific culture condition to get fungi bed for fruit body formation. Middle course of culture step is a step in which the fungi bed is cultured under the specific culture condition to achieve the formation of *Mycoleptodonoides aitchisonii* primordium. And late period of culture step is a step in which formed *Mycoleptodonoides aitchisonii* primordium is cultured under the specific culture condition to grow to fruit body. *Mycoleptodonoides aitchisonii* fruit body whose quality such as the quantity of the included component and the like are constant can be obtained by this method.

Early period of culture step is a step in which medium comprising water-keeping agent, cultivation nutrients, and water is sterilized by compression, subsequently seed-fungi of *Mycoleptodonoides aitchisonii* is inoculated and then cultured at the temperature of 15 to 35° C., preferably 21 to 27° C., humidity of 40 to 80%, preferably around 60 to 70% under dark condition, so that hyphae are spread all over the medium and nutrients for development of fruit body are accumulated on hyphae. Period of 25–90 days is preferable for maturation of the culture that is, necessary days for hyphae to spread all over the medium and for nutrients to accumulate on hyphae, is 25 to 90 days when using a bag whose volume is 1.2 kg. Generally speaking, fruit body does not develop in less than 25 days, or otherwise remarkably longer days will be needed in the following middle course of culture step. It goes without saying that days required for the early period of culture vary depending on size of culture containers used and amount of seed-fungi inoculated.

Middle course of culture step is, as aforementioned, a step in which *Mycoleptodonoides aitchisonii* primordium is formed on the fungi bed after early period of culture step. When the hyphae are cultured on the fungi bed, which is obtained at the early period of culture step, for 25 to 60 days at temperature of 8 to 22° C., preferably 12 to 16° C., at humidity of 80 to 100%, preferably 85 to 95%, and at illuminance of 50 lux or more, preferably 50 to 500 lux, *Mycoleptodonoides aitchisonii* primordium which is not exposed to physical space where it can grow to fruit body is formed, for example formed between fungi bed and container's interior etc.

Late period of culture step is, as aforementioned, a step in which *Mycoleptodonoides aitchisonii* primordium, which is not exposed to physical space where it can grow to fruit body and which is obtained at middle course of culture step, develops to fruit body. For example, when a certain area of the container, where *Mycoleptodonoides aitchisonii* primordium obtained at the middle course of culture step is not exposed to physical space where it can grow to fruit body, is taken off and *Mycoleptodonoides aitchisonii* primordium is cultured for 5 to 20 days at temperature of 8 to 22° C., preferably 12 to 16° C., at humidity of 80 to 100%, preferably 85 to 95%, at illuminance of 50 lux or more, preferably 50 to 500 lux, and under the condition that *Mycoleptodonoides aitchisonii* primordium is exposed to physical space where it can grow to fruit body, *Mycoleptodonoides aitchisonii* primordium will grow to fruit body.

Figure 1:
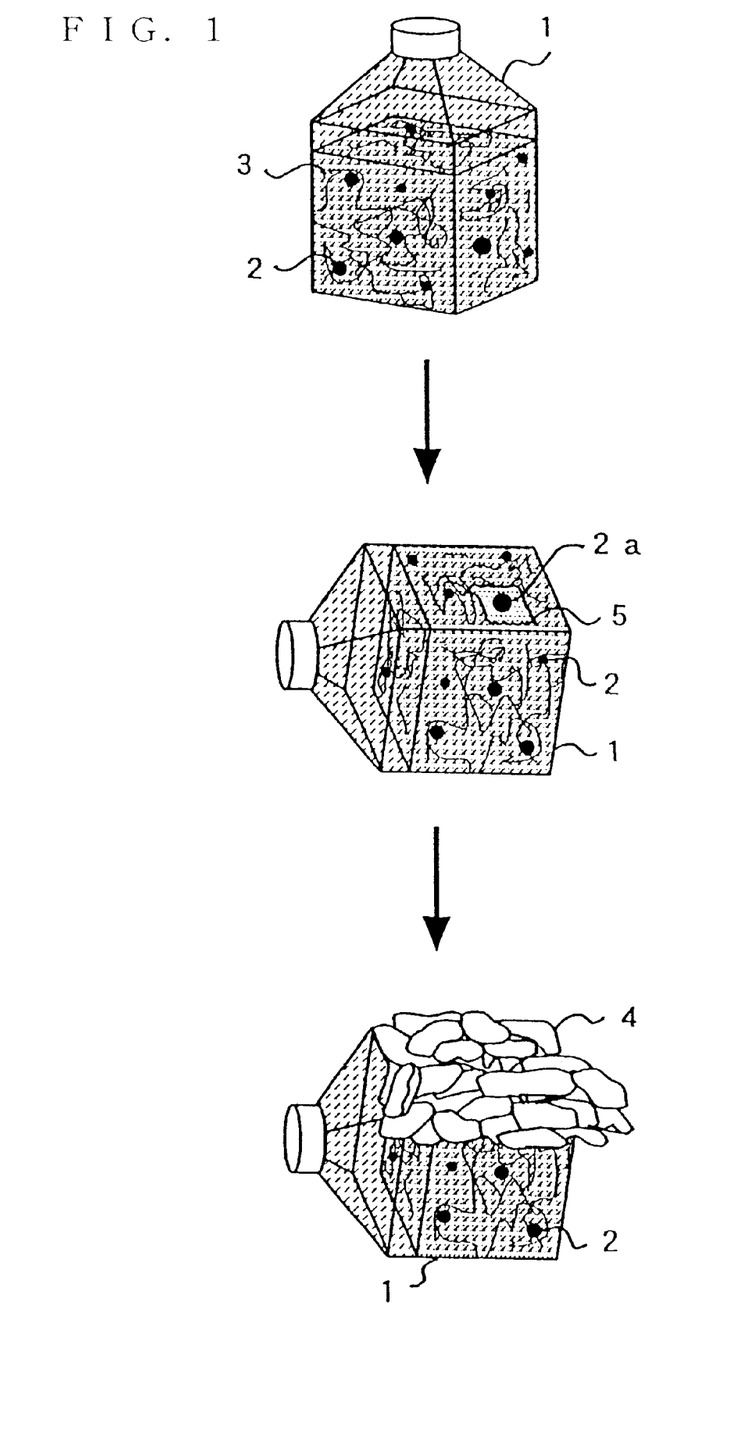
FIG. 1. An illustration to explain fungi bed cultivation method of *Mycoleptodonoides aitchisonii* in which fruit body is formed by using semi-transparent cultivation container.

Cultivation containers are generally used for cultivation of *Mycoleptodonoides aitchisonii* since, for instance, medium is easily sterilized when using them. Bags for cultivation and the like are also cultivation containers. As shown in FIG. 1, a container consists of transparent or semi-transparent material is preferable as cultivation container 1, so that formed *Mycoleptodonoides aitchisonii* primordium 2 can be eye-observed from container's outside. In order to obtain fruit body 4 larger than wild *Mycoleptodonoides aitchisonii*, it is preferable to culture one *Mycoleptodonoides aitchisonii* primordium 2a with a diameter of about 3 cm and which is selected from *Mycoleptodonoides aitchisonii* primordiums not exposed to physical space where they can grow to fruit body which are formed between fungi bed 3 and interior of cultivation container 1. Further, in order to harvest large and equal sized fruit body 4, it is preferable to culture *Mycoleptodonoides aitchisonii* primordium 2a, by laying down the cultivation container 1 which is rectangular or the like in section so that *Mycoleptodonoides aitchisonii* primordium 2a comes upside, by cutting off periphery 5 of the cultivation container where *Mycoleptodonoides aitchisonii* primordium is formed, and under the condition where *Mycoleptodonoides aitchisonii* primordium is exposed to physical space where it can grow to fruit body.

Any composition including a component having pressure reductive activity obtained from *Mycoleptodonoides aitchisonii* fruit body may used as pharmacological composition of the present invention. For example, other than extract juice or extract with pressure reductive activity obtained from *Mycoleptodonoides aitchisonii* fruit body, or composition including the extract juice or extract as an effective component, crushed *Mycoleptodonoides aitchisonii* fruit body which is crushed raw, or crushed after air-dried, hot-blast dried, or freeze-dried, and granules, capsules, and tablets made from the crushed *Mycoleptodonoides aitchisonii* fruit body by conventional methods are exemplified.

Extract juice or extract having pressure reductive activity of the present invention is obtained by extracting *Mycoleptodonoides aitchisonii* fruit body in water at room temperature, hydrothermal water, aqueous catalyst including alcohol or the like, preferably by hydrothermal extraction. Fruit body may be extracted either raw or dried for storage, but dried fruit body is preferable from a point of view of extract efficiency or easy handling or the like. Further, fruit body may be extracted as a strain or after being crushed into minute pieces. Preferable temperature at extraction is within a range of 20 to 135° C. Preferable period for extraction is 5 to 240 minutes. *Mycoleptodonoides aitchisonii* extract is obtained by concentrating and drying extract juice which has been removed of insoluble residue after hydrothermal extraction or the like, however it is preferable to perform purifying treatment after the removal of insoluble residue in manufacturing beverage. While a method to concentrate extract juice as above mentioned is not limited as long as it is a conventionally known concentration method, thermal, decompressing thermal, ethanol precipitated, and activated carbon or ion exchange resin methods for concentration and the like are concretely exemplified. Further as to drying after concentration any conventionally known method will do, but air-dry, hot-blast drying, spray dry, and freeze-dry methods and the like are concretely exemplified.

Pharmacological composition of the present invention has pressure reductive activity, at least a part of such activity is derived from intense ACE inhibiting activity, and pressure reductive activity is observed by oral injection to SHR (Spontaneous Hypertension Rat) but not by oral injection to normal rat. From this, it is expected that the pressure reductive activity only occurs in those with hypertension potential. Pharmacological composition of the present invention therefore, can be used as an agent for prevention and/or amelioration of symptom of hypertension, and as an effective ingredient for food or beverage for prevention and/or amelioration of symptom of hypertension. Further, the pharmacological composition of the present invention including component having pressure reductive activity normally brings pressure reductive activity by uptaking 100 mg to 20 g/kg weight/day as a dried fruit body, still the uptake may be fitly adjusted according to symptom, sex, and age or the like. Still further, for prevention and/or amelioration of symptom of hypertension, it can generally be used as oral medicine mixed with excipients that are pharmaceutically used in general. As described above, when pharmacological composition of the present invention is orally administrated to a normal human as prevention and/or amelioration of hypertension symptom, prevention of hypertension becomes possible, and when orally administrated to a hypertension patient, treatment of hypertension becomes possible.

Food or beverage for prevention and/or amelioration of symptom of hypertension of the present invention, characterized in that it comprises pharmacological composition of the present invention as above mentioned, may be obtained by using the pharmacological composition as an ingredient of the food/beverage materials, or by adding/combining them during or after the manufacture step. As food or beverage mentioned above, the followings are concretely exemplified: beverage such as yogurt, liquid yogurt, juice, milk, soy milk, alcohol (alcoholic drinks), coffee, black tea, green tea, oolong tea, sport drinks and the like: baked confection such as cookies, bread, cakes, and rice crackers and the like: Japanese confection such as yokan and the like: cold confection such as pudding, jelly, and ice-cream and the like: sweets such as chewing gum and candies and the like: snacks such as crackers and chips and the like: noodles such as udon and soba (Buckwheat noodles) and the like: pate-like food made from fish or meat such as kamaboko (fish cake), ham and fish sausages and the like: seasonings such as miso, soy sauce, dressings, mayonnaise, and sweetening and the like: and various dishes such as tofu, konnyaku, tsukudani (sweet cooked small fish with soy sauce), Chinese dumplings, crockets, salad, soup, and stews and the like.

The kinds of beverage including the pharmacological composition of the present invention are described in more detail hereinafter. The pharmacological composition of *Mycoleptodonoides aitchisonii* which is suitable for beverage can be obtained as extract juice by extracting *Mycoleptodonoides aitchisonii* fruit body for 30 minutes or longer, preferably about 60 minutes in hydrothermal water of 60° C. or over, preferably 90° C. or over. The hydrothermal extraction can be performed either at temperature of 100° C. or over under pressure-applied condition, or at temperature around 100° C. under normal pressure. Extraction liquid level at extract is not specifically limited, but using hydrothermal water whose weight is 10 to 20 times heavier than that of dried mushroom is preferable in aspects of such as cost and extract efficiency. Catalyst such as ethanol may be fitly added as extraction liquid, but extraction in water alone is more preferable in aspects of cost and easiness in handling at the manufacturing site. In order to improve recovery rate at the extraction, enzymes such as cellulase or peptidase may be used.

Fruit body may be extracted raw, but it is preferable to extract from dried fruit body for storage, since extract superior in quality can be obtained. Drying method is not limited provided it is a conventionally known method such as hot-blast drying method, freeze-dry method or the like, but drying method using a hot-blast drier is better for economical reason. As drying temperature for the hot-blast drying, about 60 to 70° C. is preferable. Development of burnt smell or decrease in pressure reductive activity caused by enzyme in fresh mushrooms can be repressed by drying within this temperature range. Following the drying method, it is preferable to crush fruit body before extracting for improving extraction efficiency. Mushrooms or crushed mushrooms undergo extraction while being shaken or not shaken, subsequently solid and liquid are separated by solid/liquid separation such as centrifugation or filtration, alone or combined, and then concentrated if necessary according to the above concentration methods, and the extract is prepared. The extract efficiency can be improved by performing the above extract operation for plural times.

The obtained extract juice may be added to beverage as it is, but it is most preferable to perform purifying method in order to efficiently repress development of flocks or browning etc. during storage. The purifying method is not specifically limited as long as it is a treatment after the extraction so that quality of a container packed beverage is kept and development of flocks and browning is prevented. Treatment by bentonite, alcohol, or activated carbon or the like can be concretely exemplified but bentonite or alcohol treatment is preferable in that they will not decrease the activation of pressure reductive activity of *Mycoleptodonoides aitchisonii*.

As the above bentonite treatment, a treatment is exemplified in which about 0.1 to 5 weight %, preferably about 1 weight % bentonite is added to the extract. After shaken for about 10 minutes, it is placed still for 1 hour or for several hours, then insoluble components are removed by solid/liquid separation method such as filtration or centrifugation or the like, followed by sterilization. Celite or the like may be used in solid/liquid separation as sub-agent for filtration about 1 to 5 weight %. Further, sterilization methods are exemplified such as heat sterilization for about 60 minutes at 95° C., or such as filter sterilization using membrane filter with the pore diameter of 0.45 µm capable, of preventing contaminant microbes from penetrating or the like.

As the above alcohol treatment, a treatment is exemplified in which about, for example, 25 to 200 volume % ethanol is added to the extract juice and shaken, and then placed still at room temperature for more than 1 hour. Subsequently insoluble components like high-molecular composition or the like which shows low lysis to ethanol is detected and precipitated, followed by solid/liquid separation such as Celite or the like filtration is carried out as in bentonite treatment. The ethanol is then eliminated by decompressed concentration, followed by centrifugation and sterilization.

As the activated carbon treatment, any treatment will suffice in which activated carbon treatment liquid obtained from conventionally known activated carbon treatment is sterilized. While particle-type or powder-type activated carbons may be used in the activated carbon treatment, tabular-formed activated carbon may also be used. When tabular-formed activated carbon is used for filtration., there is no need for later solid/liquid separation.

Further, these purifying treatment may be performed in any combination of the above bentonite treatment, alcohol treatment, and activated carbon treatment etc. For example, bentonite and/or activated carbon may be added to extract juice comprising ethanol, also ethanol may be added to extract juice comprising bentonite and/or activated carbon.

The purified extract juice obtained as above, may be used concentrated, but in aspect of cost, it is preferable to use at the present concentration as beverage material. In doings so, ethanol may be added from the view point of antisepsis or the like.

Combination rate of extract, when preparing kinds of beverage using the extract juice obtained by the above method as material, may be determined so that it results in excellent flavor. But if pressure reductive activity of *Mycoleptodonoides aitchisonii* is highly expected, it is preferable to include about 0.1 g to 2 g of dried weight *Mycoleptodonoides aitchisonii* extract per container beverage. In preparation of beverage kinds, any ingredients of usual prescription such as saccharide, flavor or food additives or the like may be used, and it is also used along with other functional materials such as Panax Ginseng C.A. Mayer (otane-ninjin: Japanese name), Panax Ginseng (ezoukogi: Japanese name) extract, Tasmanian blue gum extract, or Du-zhong leaf tea extract or the like. Books such as "Newly revised edition: Soft Drinks" (KORIN Co. Ltd.) can be used as a reference book concerning manufacturing method of beverage kinds. Major kinds of beverage are described hereinafter.

(Tea Beverage)

*Mycoleptodonoides aitchisonii* extract juice matches well in flavor with any kinds of tea like green tea, semi-fermented tea (oolong tea), fermented tea (black tea), especially when tea leaves of Chinese tea, especially orange osmanthus tea or Jasmine tea is used with, unique flavor of mushroom is masked. The above tea leaves may be used alone, or used along with tea leaves whose healthcare effect is promising such as Du-zhong leaf tea, persimmon leaf tea, bamboo leaf tea, gyabalong tea, corn tea, habu (seed of Ebisuso) tea, and chrysanthemum flower tea. The manufacturing method of tea leaf extract juice is not limited, still it is preferable to use more than 0.6 weight % tea leaves to mask flavor particular to mushrooms. It is preferable to separate extraction step of mushrooms and extraction step of tealeaves in order to efficiently extract pressure reductive activity component. For example, it is preferable to add/combine *Mycoleptodonoides aitchisonii* extract juice prepared separately to tea leaf extract juice.

(Nutrient Drinks)

Nutrient drinks can be manufactured by adding/combining *Mycoleptodonoides aitchisonii* extract juice at the same time of, before, or after addition/combination of ingredients that are usually used in nutrient drink manufacture. Mushroom flavor of nutrient drinks including *Mycoleptodonoides aitchisonii* has been masked by body caused by saccharide, and by characteristic flavor of mixed vitamins and of healthcare drinks.

(Fruit/vegetable Beverage)

Fruit/vegetable beverage is manufactured by selecting one or more kinds from fruit juice such as oranges, apples, grapes, peaches, strawberries, bananas or lemons or the like, or from vegetable juice such as tomatoes, carrots, cabbages, or celery or the like, and then adding/combining *Mycoleptodonoides aitchisonii* extract juice. The fruit/vegetable beverage including *Mycoleptodonoides aitchisonii* extract juice is very nice to take as mushroom flavor well Matches with fruit juice or vegetable juice.

(Carbonated Beverage)

Carbonated beverages are manufactured by adding/combining *Mycoleptodonoides aitchisonii* extract juice at the same time of, before, or after addition/combination of ingredients that are usually used in carbonate beverage manufacture. Carbon pressure of the carbonate may be set similar to carbon pressure for normal carbonated beverage (0.1 to 0.4 Mpa). Carbonated beverage in general is characterized in that its refreshing taste tends to remain in mouth after taken, so that mushroom flavor which tends to remain will be masked when added to carbonated beverage.

(Low Calorie Beverage)

Beverage with high sugar concentration is thought as a cause of obesity. Therefore, in order to delete the image, low calorie beverage is prepared in which its calorie is lowered by using super sweet sweetening such as stevioside, aspartame, sucrarose, and low calorie sweetening such as sugar alcohol like erythritol or maltitol. *Mycoleptodonoides aitchisonii* extract juice may be added/combined at any step of manufacture. And mushroom flavor can be masked by selecting flavor. Plum and litchi flavor are preferably exemplified as the flavor.

(Alcohol Beverage)

Alcohol beverage is manufactured by adding/combining *Mycoleptodonoides aitchisonii* extract juice at any step in manufacturing of alcoholic beverage such as effervescent alcoholic beverage, whiskey, or liqueur or the like. But manufacturing by adding/combining *Mycoleptodonoides aitchisonii* extract juice after brewing alcoholic beverages such as effervescent alcoholic beverage, whiskey, or liqueur or the like is preferable. Such alcoholic beverage including *Mycoleptodonoides aitchisonii* extract juice is easy to drink in that mushroom flavor has been masked.

Embodiments

The present invention is described below in more detail, but the present invention will not be limited to these embodiments.

Embodiment 1 (Fungi Bed Cultivation of *Mycoleptodonoides Aitchisonii*)

Mixture of 1,000 g in total consists of beech sawdust 380 g, dried brewer's grains 37.5 g, dried okara 37.5 g, and running water 545 g was packed in a PP (polypropylene) bag whose bulk is 1.2 kg, to prepare the medium. Subsequently the bag was capped with a polypropylene cap interleaving a filter, was pressure-sterilized for 50 minutes at 121° C. When the sterilized medium was cooled down, seed-fungi of *Mycoleptodonoides aitchisonii* were inoculated and cultured preliminarily for 40 days at temperature of 23 to 25° C., humidity of 60 to 80%, dark conditioned, and subsequently moved onto middle course of culture step. In the middle course of culture step, *Mycoleptodonoides aitchisonii* primordium was formed after 30 days of culture at temperature of 13 to 15° C., humidity of 80 to 95%, and illuminance of 200 lux. When *Mycoleptodonoides aitchisonii* primordium whose size is about 3 cm in diameter was observed in the bag, that part of the bag was cut off and the process moved onto late period of culture step. In the late period of culture step, the primordium grew to 1 strain of *Mycoleptodonoides aitchisonii* fruit body after having been cultured for 17 days under the conditions of temperature from 13 to 15° C., humidity of 80 to 95%, illuminance of 200 lux. The *Mycoleptodonoides aitchisonii* fruit body obtained weighs 232.5 g and days needed for cultivation was 87 days.

Embodiment 2 (Preparation of Extract from *Mycoleptodonoides Aitchisonii* Fruit Body)

60 g of freeze-dried and crushed *Mycoleptodonoides aitchisonii* fruit body obtained was placed in a glass container. After adding 1.5L of distilled water, it was heated for extraction for 60 minutes at 100° C., and then brown *Mycoleptodonoides aitchisonii* extract juice was obtained by eliminating *Mycoleptodonoides aitchisonii* residue. Brown extract 17.4 g was obtained by freeze-drying the extract juice. An example of physicochemical properties of the extract is shown below.

i) Color and morphology: Brown powder ii) Chemical components: Crude protein 40–45%, crude fat 0.1% or less, crude fiber 0.1–0.2%, crude ash content 10–15%, soluble non-nitrogenous content 30–40% iii) Dissolvability: water-soluble

Embodiment 3 (ACE Inhibiting Activity of the Extract)

50 mg of *Mycoleptodonoides aitchisonii* extract of Embodiment 2 was dissolved in 1 ml of distilled water and ACE inhibiting activity was analyzed. Ditilled water was used as control. The ACE inhibiting activity was tested by the method shown in the aforementioned book (Shunro Kawakishi, Methods in Biochemistry Series No. 38, "Experimental Methods for Food Factors which Contribute to Prevention of Diseases by Modulating Physiological Systems of Human Body" Japan Scientific Societies Press (JSSP), 119–121, 1996). The results are shown in Table 1. Various kinds of edible and medicinal mushrooms are treated in the same way as in Embodiment 2 for comparison, and the ACE inhibiting activity of each kind of obtained extracts were tested in the same way as above described. These results are also shown in Table 1. As shown in Table 1, the ACE inhibiting activity rate of *Mycoleptodonoides aitchisonii* extract (50 mg/ml) is 76.0%. It showed the highest inhibiting activity among mushrooms tested for comparison.

TABLE 1

| species | ACE inhibiting rate (%) |
| --- | --- |
| Mycoleptodonoides aitchisonii | 76.0 |
| Lentinus edodes | 10.7 |
| Grifola frondosa | 68.0 |
| Ganoderma Lucidum | 21.3 |
| Agaricus blazei | 14.7 |
| Hericium erinaceus pers | 28.0 |
| Chaaga | 9.3 |
| Cordyceps | 55.3 |

Embodiment 4 (Pressure Reductive Activity in SHR)

500 mg/kg of *Mycoleptodonoides aitchisonii* extract of Embodiment 2 was orally injected to SHR (spontaneous hypertension rat) and the pressure reductive activity was tested. Distilled water was used as control. The experiment was carried out for 8 rats per group both in exploratory and in control. The pressure reductive activity was tested according to below. 12 week-old male SHRs were purchased from Charles River Inc. and were pre-bred for 1 week, and orally injected with test samples or controls of various concentrations into stomach using zonde. Next, they were kept warm at 38° C. for 10 minutes at certain intervals, and then systolic pressure was measured using a device for direct measurement of pressure (Softron, BP-98). The result is shown in Table 2. Changes in pressure are not observed in control, thus in exploratory pressure starts to decrease at 2 hours after injection and showed maximum pressure reductive activity (changes in pressure being −22.4 mmHg) after 6 hours. Pressure reductive activity was also observed after 24 hours then recovered to normal pressure after 48 hours.

TABLE 2

| Time after Injection (hours) | | 0 | 2 | 4 | 6 | 8 | 10 | 24 | 48 |
|---|---|---|---|---|---|---|---|---|---|
| Control | Distilled water | 0.0 | −0.6 | −1.8 | −2.8 | −3.1 | −2.5 | −1.0 | −1.3 |
| Explatory | Extract | 0.0 | −9.0 | −21.4 | −22.4 | −21.6 | −18.1 | −14.3 | −1.8 |

Embodiment 5 (Pressure Reductive Activity in Normal Rats)

5500 mg/kg of *Mycoleptodonoides aitchisonii* extract of Embodiment 2 was orally injected into Wistar strain rats and the pressure reductive activity was measured. Distilled water was used as control. Both exploratory and control were organized as 5 rats per group. Pressure reductive activity was tested similarly as Embodiment 4 except 12 week-old male Wistar rats were used. The results are shown in Table 3. No changes in pressure were observed both in exploratory and control. From this result, it became clear that injection of *Mycoleptodonoides aitchisonii* extract has no affect on pressure of normal rats.

TABLE 3

| Time after Injection (hours) | | 0 | 2 | 4 | 6 | 8 | 10 | 24 |
|---|---|---|---|---|---|---|---|---|
| Control | Distilled water | 0.0 | 0.6 | 1.6 | −1.5 | −1.4 | 0.1 | −0.6 |
| Exploratory | Extract | 0.0 | 1.7 | 3.1 | −1.4 | −0.3 | 1.8 | −1.7 |

Embodiment 6 (Manufacturing of Beverage Including *Mycoleptodonoides aitchisonii* extract)
(Consideration of Temperature at Extraction)

*Mycoleptodonoides aitchisonii* fruit bodies harvested in Embodiment 1 were dried at 65° C. using hot-blast,drier and then crushed with a mill. With 2 g of this dried and crushed *Mycoleptodonoides aitchisonii*, extraction was carried out for 40 minutes in 40 ml of thermal water with changing temperatures at 80° C., 100° C., and 120° C. respectively, then the mixture was filtered using filter paper. The extract juice obtained was freeze-dried and measured, subsequently ACE inhibiting activity was tested using each 30 mg/ml solution of each dried extract respectively in a way similar to Embodiment 3. The result is shown in Table 4. It is preferable to extract at around 100° C. as understood from the result of Table 4.

TABLE 4

| | Extraction efficiency (%) | ACE inhibiting activity (%) |
|---|---|---|
| 80° C. | 30.4 | 39.4 |
| 100° C. | 37.6 | 58.8 |
| 120° C. | 37.2 | 56.0 |

(Consideration of Extract Time)

*Mycoleptodonoides aitchisonii* fruit bodies harvested in Embodiment 1 were dried at 65° C. using hot-blast drier and then crushed with a mill. With 2 g of this dried and crushed *Mycoleptodonoides aitchisonii*, extraction was carried out in 40 ml of thermal water at 100° C. for 20 minutes, for 40 minutes, and for 60 minutes respectively, and then the mixture was filtered with filter paper. The obtained extract juice was freeze-dried and measured, subsequently ACE inhibiting activity was tested using each 30 mg/ml solution of dried extract in a way similar as Embodiment 3. The result is shown in Table 5. It is preferable to extract for 60 minutes or longer as understood from Table 5.

TABLE 5

| | Extraction efficiency (%) | ACE inhibiting activity (%) |
|---|---|---|
| 20 min. | 29.3 | 38.3 |
| 40 min. | 29.4 | 39.4 |
| 60 min. | 36.8 | 50.6 |

(Purifying Treatment of Extract Juice)

300 g of crushed dried *Mycoleptodonoides aitchisonii* was extracted for 60 minutes in 4500 ml of boiling water, and then filtered with filter paper. The extract residue was further extracted in 3000 ml of boiling water followed by filtration with filter paper. The first filtered juice and the second filtered juice were combined together as the extract juice. The extract juice was concentrated by compressing until the juice amount is 300 ml so that crude extract is obtained. 50 ml of crude extract was heat-sterilized for 60 minutes at 95±5° C., to get extract ①.

Further, 50 ml of the above crude extract was centrifuged (3000 rpm, 5 min.), then sterilized for 60 minutes at 95±5° C. to get extract ②. 50 ml of crude extract was filtered with tabular activated carbon, and then sterilized for 60 minutes at 95±5° C., to get extract ③. 0.5 g of bentonite was added to 50 ml of crude extract and the mixture was shaken for 10 minutes, then being placed for 1 hour. After compression-filtered with a filter paper (TOYO ROSHI No. 2) which is covered with Celite whose depth being 5 mm, subsequently centrifuged (3000 rpm, 5 min.) and sterilized for 60 minutes at 95±5° C., to get extract ④. 50 ml of ethanol is added per 50 ml of crude extract and shaken, subsequently placed for 1 hour at room temperature, and then compression-filtered with a filter paper (TOYO ROSHI No. 2) covered with Celite whose depth being 5 mm. After filtration it was concentrated by compression until the volume is 50 ml, subsequently centrifuged (3000 rpm, 5 min.) and sterilized for 60 minutes at 95±5° C., to get extract ⑤. And extract ⑥ was prepared in an exactly the same way as preparation of extract ⑤ except volume of ethanol added being 100 ml.
(Evaluation of Purifying Treatment)

The above extracts ① to ⑥ were evaluated for ACE inhibiting activity, development of flocks (bottom), coloring, flavor, and included solid amount. The ACE activity was tested by the above mentioned method after diluting each extract to 1/20. As to the development of flocks (bottom), 2 ml of each extract was lysed in 180 ml of de-ionized water, then neutral (not adjusted) test liquid and acid (adjusted to pH3 with citric acid) test liquid are prepared. After being left for 1 week at room temperature, flock development was eye-measured. By defining flock of extract ① under acid condition as grade 3, extract with no flocks at all was evaluated as grade 0. As to coloring, absorbance at 420 nm was measured after leaving the above neutral (not adjusted) test liquid for 1 week at room temperature. Flavor was evaluated totally by relative evaluation of the above neutral (not adjusted) test liquid, that is, grading/evaluation was done in 5 grades and one with good flavor was graded 5 and one with bad flavor was graded 1. Solid amount included was tested by measuring solid weight per 1 ml of extract. These results are shown in Table 6. It can be determined that extracts ③ to ⑥, especially ④ and ⑤ are superior in general as understood from Table 6.

TABLE 6

| | ACE inhibiting activity | Flock development | | Coloring | Flavor | Solid amount included |
|---|---|---|---|---|---|---|
| | (%) | Neutral | Acid | | | (%) |
| Extract 1 | 55.5 | 1 | 3 | 0.155 | 2 | 27.8 |
| Extract 2 | 57.1 | 1 | 2 | 0.160 | 1 | 27.6 |
| Extract 3 | 47.1 | 0 | 1 | 0.096 | 3 | 23.7 |
| Extract 4 | 57.1 | 0 | 1 | 0.123 | 4 | 22.8 |
| Extract 5 | 54.6 | 0 | 1 | 0.116 | 4 | 21.7 |
| Extract 6 | 48.7 | 0 | 0 | 0.063 | 5 | 16.6 |

(Preparation of Tea Beverage)

Extract juice of Jasmine tea, orange osmanthus tea, black tea, and green tea that are hydrothermally extracted are adjusted with de-ionized water so that ratio of those tea leave used being 0.8 weight %. After adding equivalence of the above extract ③ to be 0.23 weight %, it was filled and packed in a bottle and sterilized by conventionally known method, to get samples 1 to 4.

(Prescription of Nutrient Drinks)

Beverage prepared according to the method below is packed in a bottle and is sterilized by conventionally known method to get sample 5.

| Equivalence of extract ⑤ | 4.0 g |
|---|---|
| Fructose dextrose liquid saccharide | 117 g |
| Galacto-oligosaccharide | 2.0 g |
| Citric acid | 3.0 g |
| Mixed vitamins | 2.6 g |
| Nutrient drink flavor | 2.0 g |
| De-ionized water | add to make the total amount 1 kg |

(Prescription of Fruit Juice Beverage)

Beverage prepared according to the method below is packed in a bottle and is sterilized by conventionally known method to get sample 6.

| Equivalence of extract ④ | 2.3 g |
|---|---|
| Suspension mixed apple juice | 900 g |
| Apple flavor | 1.0 g |
| De-ionized water | add to make the total amount 1 kg |

(Prescription of Vegetable Mixed Beverage)

Beverage prepared according to the method below is packed in a bottle and is sterilized by conventionally known method to get sample 7.

| Equivalence of extract ④ | 2.3 g |
|---|---|
| Suspension mixed apple juice | 850 g |
| Pressed celery juice | 70 g |
| Lemon juice | 20 g |
| Apple flavor | 1.0 g |
| De-ionized water | add to make the total amount 1 kg |

(Prescription of Tomato Juice)

Beverage prepared according to the method below is packed in a bottle and is sterilized by conventionally known method to get sample 8.

| Equivalence of extract ④ | 2.3 g |
|---|---|
| Pressed tomato juice | 950 g |
| De-ionized water | add to make the total amount 1 kg |

(Prescription of carbonate beverage)

Beverage prepared according to the method below is packed in a bottle and is sterilized by conventionally known method to get sample 9.

| Equivalence of extract ⑤ | 2.3 g |
|---|---|
| Fructose dextrose liquid saccharide | 114.7 g |
| Citric acid | 1.5 g |
| Mixed fruit flavor | 2.0 g |
| De-ionized water | add to make the total amount 1 kg |

(Carbon Gas Pressure is Adjusted to 0.15 Mpa)

(Prescription of Low Calorie Beverage)

Beverage prepared according to the method below is packed in a bottle and is sterilized by conventionally known method to get sample 10.

| Equivalence of extract ④ | 2.3 g |
|---|---|
| Erythritol | 17.0 g |
| Stevioside | 0.19 g |
| Citric acid | 0.60 g |
| Plum flavor | 1.5 g |
| De-ionized water | add to make the total amount 1 kg |

(Sensor Test for Samples 1 to 10)

Taste of above samples 1 to 10 were evaluated by 15 expert panelists. Equivalence of extract ① was added into de-ionized water as to be 0.23 weight % for control. When a sample was thought very tasty in comparison with the control, it was graded as 5 and when thought as very bad tasted, it was graded −5, and the standard was calculated. All the samples 1 to 10 had more palatability than control. The result is shown in Table 7.

TABLE 7

| | Grades |
|---|---|
| Sample 1 | 2.1 |
| Sample 2 | 1.7 |
| Sample 3 | 0.9 |
| Sample 4 | 1.2 |
| Sample 5 | 2.1 |
| Sample 6 | 2.5 |
| Sample 7 | 2.6 |
| Sample 8 | 0.6 |
| Sample 9 | 3.3 |
| Sample 10 | 2.3 |

(Animal Evaluation Experiment for Samples 1 to 10)

An experiment was carried out using rats for samples 2, 5, and 6. 3 ml/kg each of sample 2 and 6, and 1.67 ml/kg of sample 5 were orally injected to SHR (Spontaneous Hypertension Rat) respectively and pressure reductive activity was measured. Distilled water was used as control. The experiment was performed with 6 rats per group in both exploratory and control. The pressure reductive activity was measured according to the method as follows: 12 week-old male SHRs were purchased from Charles River Inc and pre-bred for 1 week. Then the SHRs were orally injected with each sample into stomach with zonde followed by measurement of systolic pressure at 4 hour and 6 hour after the injection using a device for direct measurement of pressure (Softron, BP-98). For 10 minutes before the measurement, rats were kept warm at 38° C. The results are shown in Table 8. It was confirmed that exploratory group has statistically significantly more pressure reductive activity than control group from Table 8. As seen from the above results, the same effect will be anticipated for a human whose weight is 60 kg by taking 180 ml of samples 2 and 6, and 100 ml of sample 5.

TABLE 8

| | Changes of systolic pressure (mmHg) | | |
|---|---|---|---|
| | Before injection | After 4 hours | After 6 hours |
| Distilled water | 0.0 | −1.2 | −2.1 |
| Sample 2 | 0.0 | −8.1 | −5.6 |
| Sample 5 | 0.0 | −6.6 | −4.8 |
| Sample 6 | 0.0 | −14.9 | −14.6 |

(Prescription of Alcoholic Beverages)

Effervescent alcoholic beverage with less than 25% of malt included (alcoholic concentration 5.5 v/v%) was brewed according to conventionally known method and equivalence of above extract ③ was added to be 0.11 weight %, and then packed in a bottle to make sample 11. This sample 11 was sensor tested by 9 expert panelists. As control, equivalence of extract ① was added to de-ionized water to be 0.23 weight %. Sample 11 had more palatability than control. Further when compared to normal effervescent alcoholic beverage which does not include equivalence of extract ③, some sweet scent was felt but no difference in flavor was confirmed.

(Experiment of Animal Evaluation for Sample 11)

Test was performed for sample 11 using 26 week-old male SHRs (Spontaneous Hypertension Rats). Sample 11 was orally injected as, 5.83 ml/kg and pressure reductive activity was measured. Distilled water and effervescent alcoholic beverage not including above extract ③ was used as control. The experiment was performed with 6 rats per group both in exploratory and control and pressure reductive activity was tested. Then the SHRs were orally injected with each sample into stomach by zonde followed by measurement of systolic pressure at 6 hour after the administration using a device for direct measurement of pressure (Softron, BP-98). For 10 minutes before the measurement, rats were kept warm at 38° C. The results are shown in Table 9. It was confirmed that exploratory group has statistically significantly more pressure reductive activity than control group from Table 9. As seen from the above results, the same effect can be expected for a human whose weight is 60 kg by taking 350 ml of sample 11.

TABLE 9

| | Changes of systolic pressure (mmHg) | |
|---|---|---|
| | Before injection | After 6 hours |
| Distilled water | 0.0 | 0.5 |
| Effervescent alcohol | 0.0 | −0.5 |
| Sample 11 | 0.0 | −14.1 |

Effect of the Invention

The pharmacological composition of the present invention having component with pressure reductive activity obtained from *Mycoleptodonoides aitchisonii* shows pressure reductive activity only to hypertension model animals and not to normal model animals, so that it is useful as safe pressure reductive active agent. Further by using artificial cultivation product of *Mycoleptodonoides aitchisonii* fruit body as a material, pharmacological composition such as fruit body extract juice and extract and the like at low cost and with equal quality can be produced constantly year-round. Further, beverages manufactured by using pharmacological composition of the present invention can repress development of such as flocks and browning, while keeping pressure reductive activity.

EXPLANATION OF NUMERALS

1. Cultivation container for *Mycoleptodonoides aitchisonii*
2, 2a. *Mycoleptodonoides aitchisonii* primordium
3. fungi bed
4. Mycoleptodonoides aitchisoniifruit body
5. Periphery of where *Mycoleptodonoides aitchisonii* primordium is formed.

What is claimed:

1. A pharmacological composition comprising an aqueous extract obtained at a temperature of at least about 60° C. from *Mycoleptodonoides aitchisonii* fruit body obtained by artificial cultivation, said composition having blood pressure reductive activity.

2. The pharmacological composition of claim 1 wherein the fruit body is a dried fruit body.

3. The pharmacological composition of claim 1 wherein said extract is juice.

4. The pharmacological composition of claim 1 wherein said extract is obtained by hydrothermal extraction of the fruit body.

5. The pharmacological composition of claim 4 wherein the extract is further purified after hydrothermal extraction.

6. The pharmacological composition of claim 5 wherein the extract is further purified by bentonite treatment and/or alcohol treatment.

7. The pharmacological composition of claim 1 wherein the artificial cultivation is fungi bed cultivation.

8. The pharmacological composition of claim 7 wherein said fungi bed cultivation consists of
   i) obtaining a sterilized medium comprising a water-keeping agent, a culture substrate comprising at least one nutrient selected from dried okara or brewer's yeast, and water;
   ii) inoculating seed-fungi of *Mycoleptodonoides aitchisonii* into the sterilized medium to obtain an inoculated medium;
   iii) culturing the inoculated medium to obtain a fungi bed wherein hyphae have grown on said medium;
   iv) obtaining *Mycoleptodonoides aitchisonii* primordium, from the culture of the fungi bed, wherein said primordium has not been exposed to physical space where it can grow into a fruit body; and
   v) culturing the primordium under conditions with sufficient physical space to grow into a fruit body;
   to obtain *Mycoleptodonoides aitchisonii* fruit body.

9. The pharmacological composition of claim 1, wherein at least a part of the blood pressure reductive activity is due to inhibition of angiotensin I converting enzyme.

10. A food or beverage for prevention and/or amelioration of hypertension that contains the pharmacological composition of claim 1.

11. The food or beverage of claim 10 that is selected from the group consisting of a tea beverage, a nutrient drink, a fruit/vegetable beverage, a carbonated beverage, a low-calorie beverage, and an alcoholic beverage.

12. A method of preventing hypertension comprising orally administering the pharmacological composition according to claim 1 to a normal human.

13. A method of treating hypertension comprising orally administering the pharmacological composition according to claim 1 to a hypertension patient.

* * * * *